US012788289B2

(12) United States Patent
Burkholz et al.

(10) Patent No.: US 12,788,289 B2
(45) Date of Patent: Nov. 10, 2026

(54) CATHETER SYSTEM HAVING AN EXTENSION SET FOR BLOOD SAMPLING

(71) Applicant: Becton, Dickinson and Company, Franklin Lakes, NJ (US)

(72) Inventors: Jonathan Karl Burkholz, Salt Lake City, UT (US); Erica E. Neumann, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 552 days.

(21) Appl. No.: 18/238,970

(22) Filed: Aug. 28, 2023

(65) Prior Publication Data

US 2024/0082547 A1 Mar. 14, 2024

Related U.S. Application Data

(60) Provisional application No. 63/405,703, filed on Sep. 12, 2022.

(51) Int. Cl.
*A61B 5/15* (2006.01)
*A61B 5/153* (2006.01)
(Continued)

(52) U.S. Cl.
CPC .... *A61B 5/15003* (2013.01); *A61B 5/150221* (2013.01); *A61B 5/150251* (2013.01); *A61B 5/150992* (2013.01); *A61B 5/153* (2013.01); *A61M 25/0097* (2013.01); *A61M 25/0606* (2013.01); *A61M 39/105* (2013.01); *A61M 39/223* (2013.01); *A61M 2025/0001* (2013.01); *A61M 25/0637* (2013.01); *A61M 2230/30* (2013.01)

(58) Field of Classification Search
CPC .......... A61M 25/0606; A61M 25/0097; A61M 2039/1077; A61M 39/223; A61M 39/10; A61M 2039/229; A61M 25/0693; A61M 39/105; A61M 39/22; A61M 2005/1403; A61M 25/0637; A61M 2025/0001; A61M 2230/30; A61B 5/15003; A61B 5/150992; A61B 5/150221; A61B 5/153; A61B 5/150251
See application file for complete search history.

(56) References Cited

U.S. PATENT DOCUMENTS

| | | | | | |
|---|---|---|---|---|---|
| 4,819,653 | A * | 4/1989 | Marks | A61B 5/0215 | 600/561 |
| 5,002,528 | A * | 3/1991 | Palestrant | A61M 1/70 | 604/246 |

(Continued)

FOREIGN PATENT DOCUMENTS

WO 2022098589 A1 5/2022

*Primary Examiner* — Wesley G Harris
(74) *Attorney, Agent, or Firm* — Kirton McConkie; Whitney Blair; Kevin Stinger

(57) ABSTRACT

A catheter system may include a catheter adapter, which may include a side port. The catheter system may include a catheter, and an extension tube having a distal end and a proximal end. The catheter system may include a three-port connector, which may include a distal port, a proximal port, and a side port. The proximal end of the catheter adapter may be coupled to the distal port of the three-port connector. The distal end of the extension tube may be integrated with the side port of the three-port connector.

20 Claims, 17 Drawing Sheets

(51) Int. Cl.

| | |
|---|---|
| ***A61M 25/00*** | (2006.01) |
| ***A61M 25/06*** | (2006.01) |
| ***A61M 39/10*** | (2006.01) |
| ***A61M 39/22*** | (2006.01) |

(56) References Cited

U.S. PATENT DOCUMENTS

| | | | | |
|---|---|---|---|---|
| 5,807,312 | A * | 9/1998 | Dzwonkiewicz ... | A61M 5/1424<br>604/32 |
| 11,191,939 | B2 | 12/2021 | Funk | |
| 2012/0065502 | A1* | 3/2012 | Levy ........................ | A61M 5/19<br>600/431 |
| 2015/0011910 | A1 | 1/2015 | Bullington et al. | |
| 2020/0078564 | A1* | 3/2020 | Blanchard ......... | A61M 25/0606 |
| 2020/0230315 | A1* | 7/2020 | Ma ...................... | A61M 5/1452 |
| 2020/0230353 | A1 | 7/2020 | Burkholz et al. | |
| 2021/0085927 | A1 | 3/2021 | Howell | |

* cited by examiner

CATHETER SYSTEM HAVING AN EXTENSION SET FOR BLOOD SAMPLING

RELATED APPLICATIONS

This application claims the benefit of U.S. Provisional Patent Application No. 63/405,703, which was filed on Sep. 12, 2022, which is incorporated herein in its entirety.

BACKGROUND

Arterial catheterization is a vital procedure that is used ubiquitously in the hospital setting, both in critically injured and perioperative patients. It is estimated that more than eight million arterial catheters are placed yearly in the United States. Arterial catheters can continuously and accurately measure blood pressure as well as heart rate and pulse contour to allow for immediate recognition of aberrant hemodynamic events and initiation of appropriate treatment. Arterial catheters also provide samples for blood gas analysis without the morbidity associated with repeat arterial puncture. However, use of current arterial catheters can result in significant blood leakage during insertion into an artery of a patient, which can endanger a user. Moreover, current arterial catheters may be difficult to secure, maintain, and flush.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices, systems, and methods. In particular, the present disclosure relates to a catheter system configured for blood sampling, such as, for example, arterial blood sampling, as well as related devices and methods. In some embodiments, the catheter system may also be configured for blood pressure monitoring and/or blood gas sampling. Importantly, in some embodiments, the catheter system may provide near-patient access for more accurate hemodynamic measurements and improved delivery of an instrument, such as a secondary catheter and/or a sensor, into a blood vessel, which may include an artery or a vein. In some embodiments, the catheter system may include a guidewire for improved catheter insertion success. In some embodiments, the catheter system may reduce blood exposure when inserted the catheter into an artery of a patient.

In some embodiments, the catheter system may include a catheter adapter, which may include a distal end, a proximal end, a lumen extending through the distal end of the catheter adapter and the proximal end of the catheter adapter. In some embodiments, the catheter system may include a catheter extending from the distal end of the catheter adapter.

In some embodiments, the catheter system may include a three-port connector, which may be configured to provide near-patient access. In some embodiments, the three-port connector may include a distal port, a proximal port, and a side port between the distal port and the proximal port. In some embodiments, the three-port connector may include more than three ports. In other embodiments, the three-port connector may include exactly three ports. In some embodiments, the distal port and the proximal port may be aligned with a longitudinal axis of the three-port connector. In some embodiments, the side port and/or an extension tube may be angled at 90° with respect to the longitudinal axis of the three-port connector or between 15° to 165° with respect to the longitudinal axis of the three-port connector. In some embodiments, the proximal end of the catheter adapter may be coupled to the distal port of the three-port connector.

In some embodiments, the catheter system may include the extension tube, which may include a distal end and a proximal end. In some embodiments, the distal end of the extension tube may be integrated with the side port of the three-port connector. In some embodiments, the proximal port may include a connector, which may facilitate coupling of a blood sampling device to the three-port connector. In some embodiments, the proximal port may include another suitable connector. In some embodiments, the blood sampling device may be coupled to the proximal port. In some embodiments, the blood sampling device may include a catheter advancement device such as, for example, the PIVO™ Needle-Free Blood Collection Device, available from Becton, Dickinson & Company of Franklin Lakes, New Jersey. In some embodiments, the blood sampling device may include another suitable blood sampling device.

In some embodiments, the catheter system may include a three-way stopcock valve, which may include a first port, a second port opposite the first port, and a third port. In some embodiments, the third port may be perpendicular to the first port and the second port. In some embodiments, the proximal end of the extension tube may be coupled to the first port of the three-way stopcock valve. In some embodiments, the proximal end of the extension tube may be integrated with the first port, which may reduce a risk of fluid exposure to a user.

In some embodiments, the catheter system may include a fluid pathway within at least the catheter, the catheter adapter, the three-port connector, and the extension tube. In some embodiments, the second port, the third port, and the proximal port of three-port connector may be configured to provide access to the fluid pathway of the catheter system. In some embodiments, the catheter system may include one or more other access points to the fluid pathway from a surrounding environment. In some embodiments, the catheter system may not include other access points to the fluid pathway from a surrounding environment, which may limit potential bacterial contamination. In some embodiments, the proximal port may be used for near-patient blood sample collection, the second port may be used to facilitate line clearance with a single flush, and the third port may be used for temporarily withdrawing blood from the patient to ensure a high-quality sample.

In some embodiments, the catheter system may include a pre-filled flush device coupled to the second port such that closing of the second port, such as by rotating a central hub of the three-way stopcock valve, prevents fluid communication between the pre-filled flush device and the fluid pathway. In some embodiments, a temporary discard sample syringe may be coupled to the third port such that closing of the third port, such as by rotating the central hub of the three-way stopcock valve, prevents fluid communication between the temporary discard sample syringe and the fluid pathway. In some embodiments, the temporary discard sample syringe may be configured for temporary blood withdrawal.

In some embodiments, the catheter system may include a pressure transducer. In some embodiments, the pressure transducer may be disposed between the second port and the pre-filled flush device, which may facilitate flushing of the catheter system via a single flush.

In some embodiments, the proximal end of the extension tube may be integrated with an adapter, which may be configured to couple to one or more of the pre-filled flush device, the temporary discard sample syringe, and the three-way stopcock valve. In some embodiments, the adapter may be coupled to a needleless connector, which may reduce a risk of bacterial contamination. In some embodiments, a proximal end of the adapter may include a single port or a dual port.

In some embodiments, the catheter system may be compact, easing usage, and may improve workflow when collecting an arterial or venous blood sample. In some embodiments, a method of blood collection may include coupling the pre-filled flush device and the temporary discard sample syringe to the catheter system and closing the second port. In some embodiments, after closing the second port, the method may include pulling blood into the temporary discard sample syringe. In some embodiments, after pulling blood into the temporary discard sample syringe, the method may include closing the first port. In some embodiments, after closing the first port, the method may include collecting blood in the blood sampling device, which may be coupled to the proximal port of the three-port connector. In some embodiments, the blood sampling device may include a heparinized syringe, and blood may then be dispensed to an arterial blood gas (ABG) test cartridge for point of care (POC) blood testing.

In some embodiments, the blood sampling device may include a catheter advancement device. In some embodiments, the method may include advancing a secondary catheter and/or a sensor of the catheter advancement device through the catheter of the catheter system. In some embodiments, after collecting blood in the blood sampling device coupled to the proximal port of the three-port connector, the method may include closing the second port another time. In some embodiments, after closing the second port the other time, the method may include returning the blood pulled into the temporary discard syringe into a patient.

In some embodiments, after returning the blood pulled into the temporary discard syringe into the patient, the method may include turning the three-way stopcock valve to an open position and activating the pre-filled flush device to clear the catheter system with a single flush. In some embodiments, the catheter system may include the pressure transducer, which may be disposed between the second port and pre-filled flush device or another suitable location.

In some embodiments, a method of blood collection may include inserting the catheter system into a blood vessel of a patient. In some embodiments, the method may include advancing a secondary catheter of a catheter advancement device through the catheter. In some embodiments, the catheter advancement device may be coupled to the proximal port of the three-port connector. In some embodiments, the blood vessel may be an artery.

In some embodiments, the catheter system further comprises a pressure transducer, which may be disposed between the second port and pre-filled flush device. In some embodiments, the method may include monitoring arterial blood pressure via the pressure transducer while or at a same time as advancing the secondary catheter of the catheter advancement device through the catheter. In some embodiments, the method may include coupling the pre-filled flush device to the pressure transducer and activating the pre-filled flush device such that fluid from the pre-filled flush device flows through the pressure transducer.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Referring now to FIGS. 1A-2A, in some embodiments, a catheter system 10 may be configured for blood sampling, such as, for example, arterial blood sampling. In some embodiments, the blood sampling may be used for determination of blood gas content. In some embodiments, the catheter system 10 may also be configured for blood pressure. Importantly, in some embodiments, the catheter system 10 may provide near-patient access for more accurate hemodynamic measurements and improved delivery of an instrument, such as a secondary catheter and/or a sensor, into a blood vessel, which may include an artery or a vein.

In some embodiments, the catheter system 10 may include an arterial catheter system configured for insertion into an artery. In these embodiments, the catheter system 10 may include significant improvements to existing arterial catheter systems by dramatically reducing blood exposure and infection risk, providing a user with improved artery access confirmation, and improving an overall experience of a patient. Some existing arterial catheter systems, such as, for example, the Teleflex ARROW® Integrated Arterial Catheter, may not provide effective artery access confirmation or blood control, which may result in placement procedures with significant blood exposure risk, infection risk, clean-up costs, and poor patient experience. The Teleflex ARROW® Integrated Arterial Catheter includes a non-rigid, slotted tube out of which significant amounts of blood may leak, increasing the risk of blood exposure to the user. The catheter system 10 may include one or more of the following, which may provide advantages over the prior art: arterial blood sampling with reduced blood exposure; blood pressure monitoring; blood gas sampling; near-patient access for use of a secondary catheter and/or sensor; blood control configured to operate under arterial pressure; a guidewire; and magnetic introducer needle guidance technology.

Figure 1A:
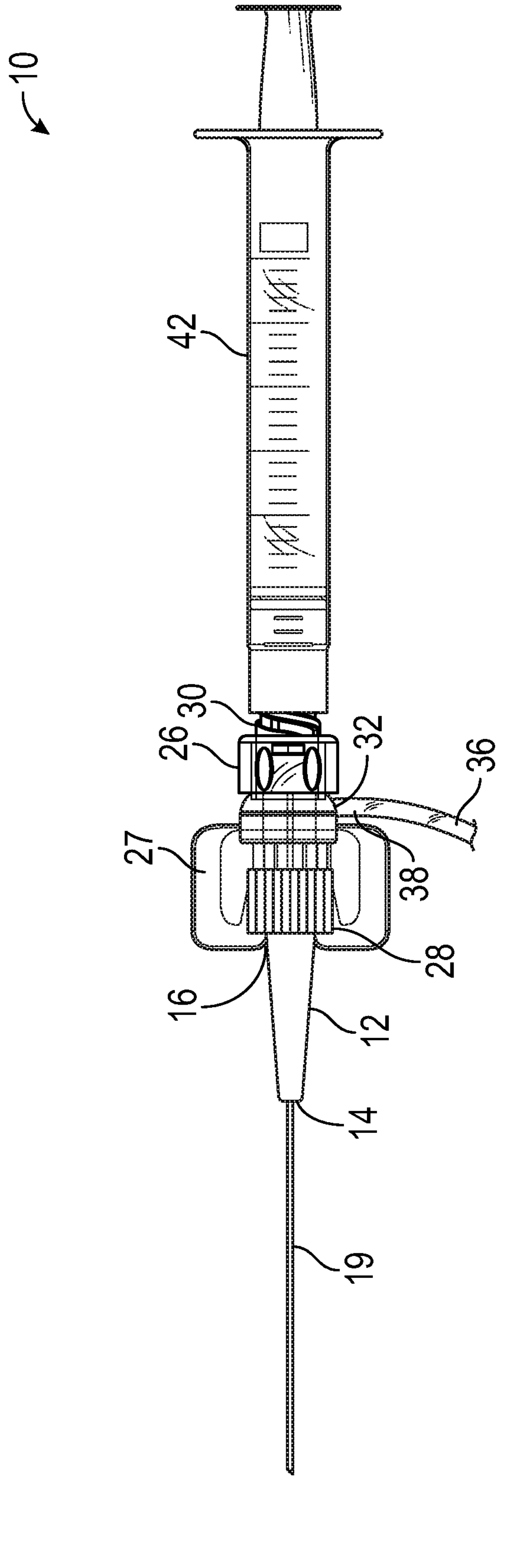
FIG. 1A is an upper perspective view of an example catheter system, according to some embodiments.

As illustrated in FIG. 1A, in some embodiments, the catheter system 10 may include a catheter adapter 12, which may include a distal end 14, a proximal end 16, a lumen extending through the distal end 14 of the catheter adapter 12 and the proximal end 16 of the catheter adapter 12. In some embodiments, the catheter system 10 may include a catheter 19 extending from the distal end 14 of the catheter adapter 12. In some embodiments, the catheter 19 may include an arterial catheter, a peripherally-inserted central catheter, a midline catheter, a peripheral intravenous catheter, or another suitable catheter.

In some embodiments, the catheter system 10 may include an introducer needle coupled to a needle hub. In some embodiments, the catheter 19 may include an "over-the-needle" catheter, and the introducer needle may extend through the catheter 19 to assist in insertion of the catheter 19 into the blood vessel of the patient. In some embodiments, after the catheter 19 is inserted into the blood vessel (which may be confirmed by the user through visualization of blood in a flashback chamber or INSTAFLASH™), the needle hub may be uncoupled from the catheter adapter 12, and the introducer needle may be removed. In some embodiments, the catheter adapter 12 may include blood control technology, such as a septum, which may prevent blood leakage from the catheter adapter 12 after removal of the introducer needle.

In some embodiments, the catheter system 10 may include a three-port connector 26, which may be configured to provide near-patient access. In some embodiments, the three-port connector 26 may include a distal port 28, a proximal port 30, and a side port 32 between the distal port 28 of the three-port connector 26 and the proximal port 30 of the three-port connector 26. In some embodiments, the distal port 28 and the proximal port 30 may be aligned with a longitudinal axis 34 of the three-port connector 26.

In some embodiments, the catheter system 10 may include an extension tube 36, which may include a distal end 38 and a proximal end 40. In some embodiments, the distal end 38 of the extension tube 36 may be integrated with the side port 32 of the three-port connector 26, which may reduce a risk of fluid exposure to the user. In further detail, in some embodiments, the distal end 38 of the extension tube 36 may be permanently or non-removably coupled to the side port 32, such as, for example, via adhesive, bonding, a non-luer coupling, or another suitable permanent or non-removable coupling.

In some embodiments, the side port 32 and/or the extension tube 36 may be angled at about 90° with respect to the longitudinal axis 34 of the three-port connector 26 and may form a T-shape or T-connector. In these and other embodiments, the three-port connector 26 may be similar or identical in terms of one or more features and/or operation to one or more stabilizing connectors further described in U.S. Pat. No. 11,191,939, filed Nov. 30, 2018, entitled "STABILIZING CONNECTOR DEVICES FOR VASCULAR ACCESS AND METHODS OF USING THE SAME," which is hereby incorporated by reference in its entirety. In some embodiments, the T-shape may facilitate flushing of the catheter assembly 10 when flushed from the proximal end 40 of the extension tube 36. In some embodiments, the side port 32 and/or the extension tube 36 may be angled at less than or greater than 90° with respect to the longitudinal axis 34, which may form a Y-shape. In some embodiments, the side port 32 and/or the extension tube 36 may be angled between 15° to 165° with respect to the longitudinal axis 34 of the three-port connector 26, such that the extension tube 36 extends in a distal direction or a proximal direction. In some embodiments, the side port 32 may be on a left side or a right side of the three-port connector 26 and/or may be configured to direct the extension tube 36 away from an insertion site of the catheter into the blood vessel. In some embodiments, the proximal end 16 of the catheter adapter 12 may be coupled to the distal port 28 of the three-port connector 26.

In some embodiments, the catheter system 10 may be a non-integrated catheter system, meaning that the catheter system does not include extension tubing (e.g., an extension set) extending from a side port of the catheter adapter 12 that provides a fluid pathway to the catheter 19. In some embodiments, the three-port connector 26 may instead provide an extension set that includes the extension tube 36.

Figure 1B:
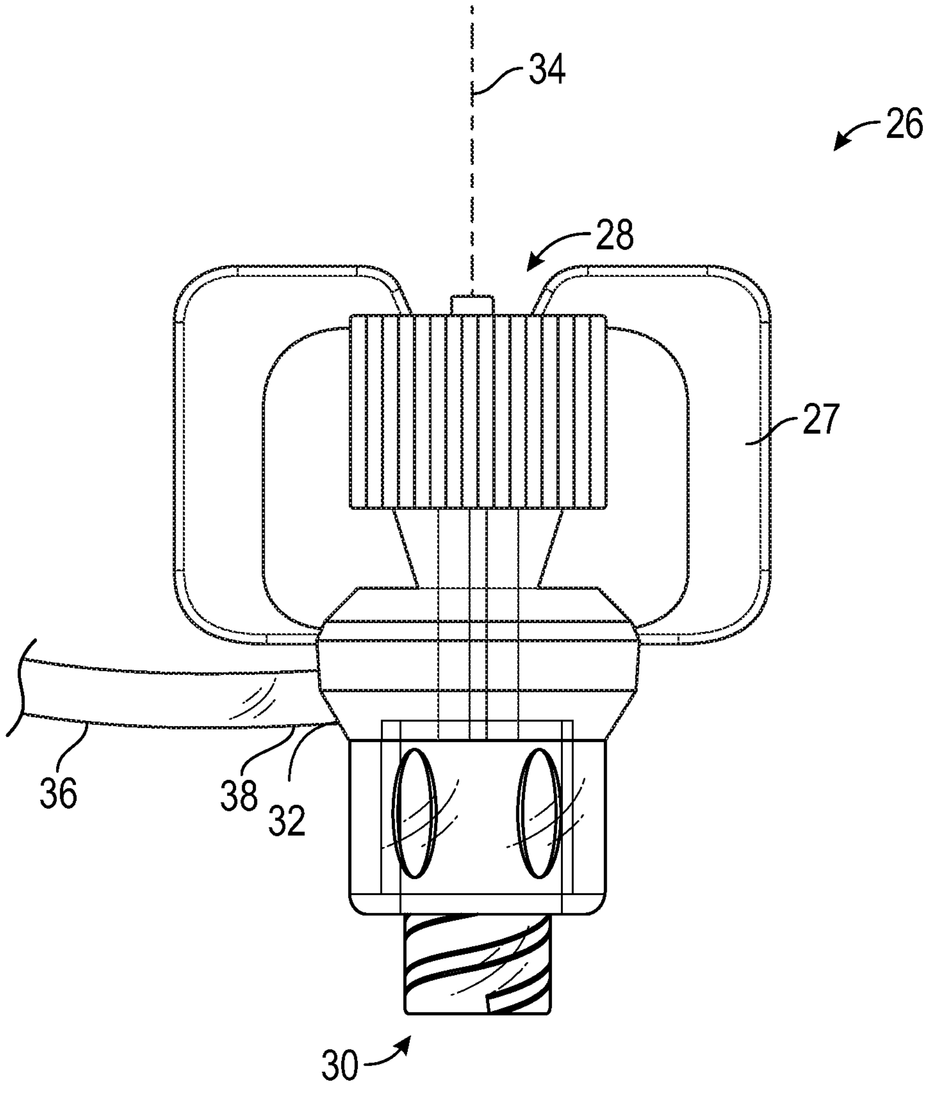
FIG. 1B is an upper perspective view of an example three-port connector, according to some embodiments.
Figure 2A:
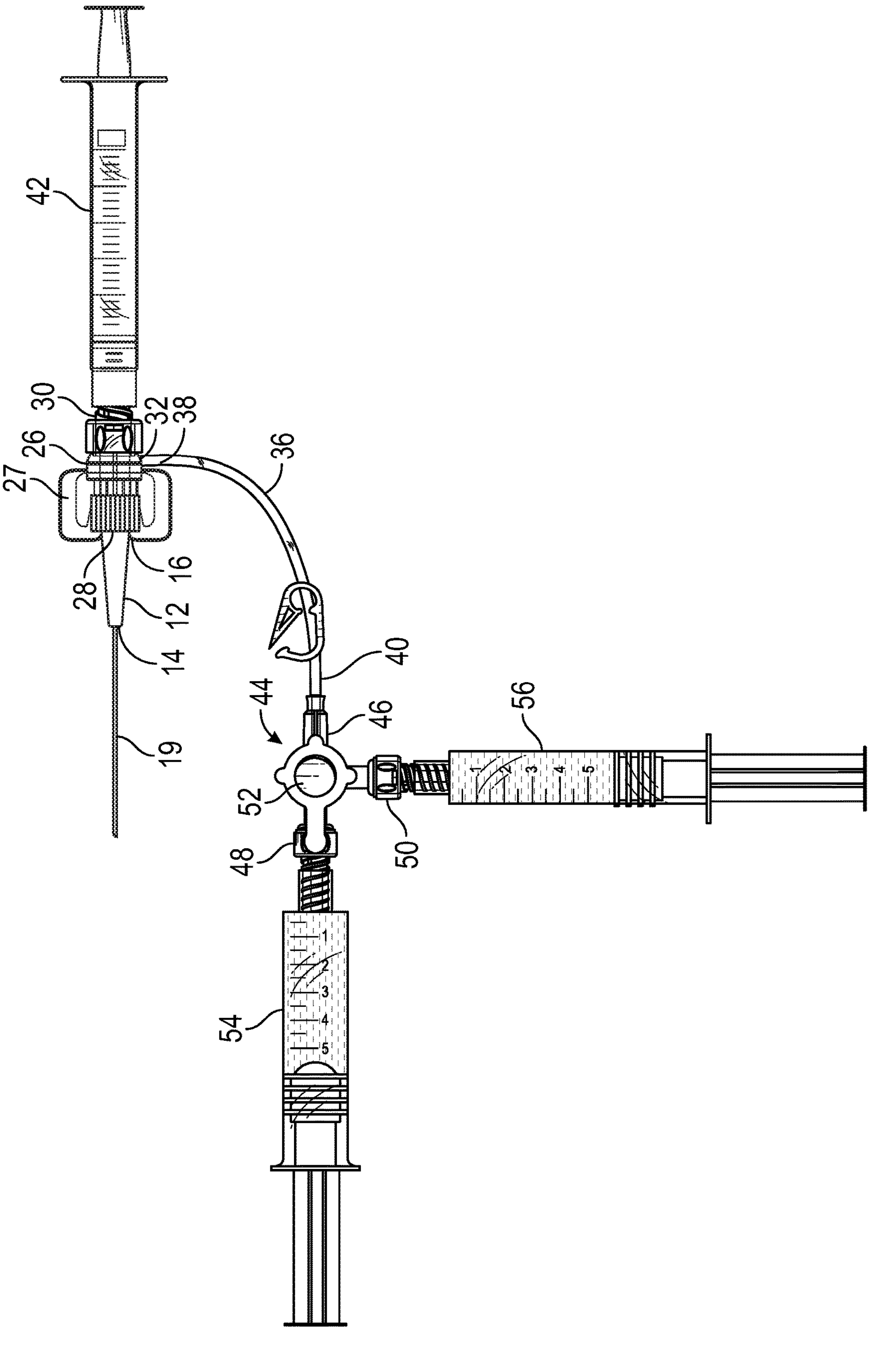
FIG. 2A is an upper perspective view of the catheter system, illustrating an example three-way stopcock valve, an example pre-filled flush device, and an example temporary discard sample syringe, according to some embodiments.

As illustrated in FIGS. 1A-1B, in some embodiments, the proximal port 30 may include a connector, which may facilitate coupling of a blood sampling device to the three-port connector 26. In some embodiments, the connector of the proximal port 30 may include a female luer or another type of connector. In some embodiments, the connector of the proximal port 30 may be integrated with the three-port connector 26. In further detail, in some embodiments, the connector of the proximal port 30 may be permanently or non-removably coupled to the three-port connector, such as, for example, via adhesive, bonding, a non-luer coupling, or another suitable permanent or non-removable coupling. In some embodiments, the connector may be monolithically formed as a single unit with the three-port connector 26. As illustrated in FIG. 2A, in some embodiments, the blood sampling device 42 may be coupled to the proximal port 30. In some embodiments, the proximal port 30 may be colored red to indicate the proximal port 30 provides access to an artery. In some embodiments, the blood sampling device 42 may include a vacuum tube or a syringe. In some embodiments, the blood sampling device 42 may include a probe and/or a sensor. In some embodiments, the blood sampling device 42 may include a catheter advancement device such as, for example, the PIVO™ Needle-Free Blood Collection Device, available from Becton, Dickinson & Company of Franklin Lakes, New Jersey. In some embodiments, the blood sampling device 42 may include another suitable blood sampling device. In some embodiments, the blood sampling device 42 may be configured to advance the secondary catheter and/or the sensor through the straight path and/or through the catheter 19 into a blood vessel of the patient, such as an artery, for example.

In some embodiments, the catheter system 10 may include a three-way stopcock valve 44, which may include a first port 46, a second port 48 opposite the first port 46, and a third port 50. In some embodiments, a central hub 52 of the three-way stopcock valve 44 may be rotated to selectively open or close fluid flow through the first port 46, the second port 48, and the third port 50, as is known in the art. In some embodiments, the proximal end 40 of the extension tube 36 may be coupled to the first port 46 of the three-way stopcock valve 44. In some embodiments, the proximal end 40 of the extension tube 36 may be integrated with the first port 46, which may reduce a risk of fluid exposure to the user. In further detail, in some embodiments the proximal end 40 of the extension tube 36 may be permanently or non-removably coupled to the first port 46, such as, for example, via adhesive, bonding, a non-Luer coupling, or another suitable permanent or non-removable coupling. In some embodiments, the second port 48 and/or the third port 50 may include luers, such as, for example, female luers, which may facilitate coupling to a device.

In some embodiments, the catheter system 10 may include a fluid pathway within at least the catheter 19, the catheter adapter 12, the three-port connector 26, and the extension tube 36. In some embodiments, the second port 48, the third port 50, and the proximal port 30 of three-port connector 26 may be configured to provide access to the fluid pathway of the catheter system 10. In some embodiments, the catheter system 10 may include one or more other access points to the fluid pathway from a surrounding environment. In some embodiments, the catheter system 10 may not include other access points to the fluid pathway from a surrounding environment, which may limit potential bacterial contamination.

In some embodiments, one or more of the second port 48, the third port 50, and the proximal port 30 may be non-removable and/or monolithically formed as a single unit with a body of the three-way stopcock valve 44 in which the central hub 52 rotates. In some embodiments, one or more of the second port 48, the third port 50, and the proximal port 30 may include a removable needleless connector coupled to a non-removable portion of the respective port. In some embodiments, needleless connector may reduce a risk of bacterial contamination. In some embodiments, the proximal port 30 may be used for near-patient access, including blood sample collection. In some embodiments, the second port 48 may be used to facilitate clearance of the catheter system 10, including the fluid pathway, with a single flush, and the third port 50 may be used for temporarily withdrawing blood from the patient to ensure a high-quality sample. In some embodiments, one or more of the adapter 58, the first port 46, the second port 48, and the third port 50 may include a vent plug or an end cap.

In some embodiments, the catheter system 10 may include a pre-filled flush device 54 coupled to the second port 48 such that closing of the second port 48, such as by rotating the central hub 52 of the three-way stopcock valve 44, prevents fluid communication between the pre-filled flush device 54 and the fluid pathway. In some embodiments, the pre-filled flush device 54 may include a pre-filled flush syringe, an IV line, or another suitable device. In some embodiments, a temporary discard sample syringe 56 may be coupled to the third port 50 such that closing of the third port 50, such as by rotating the central hub 52 of the three-way stopcock valve 44, prevents fluid communication between the temporary discard sample syringe 56 and the fluid pathway. In some embodiments, the temporary discard sample syringe 56 may be configured for temporary blood withdrawal from the patient.

Figure 2B:
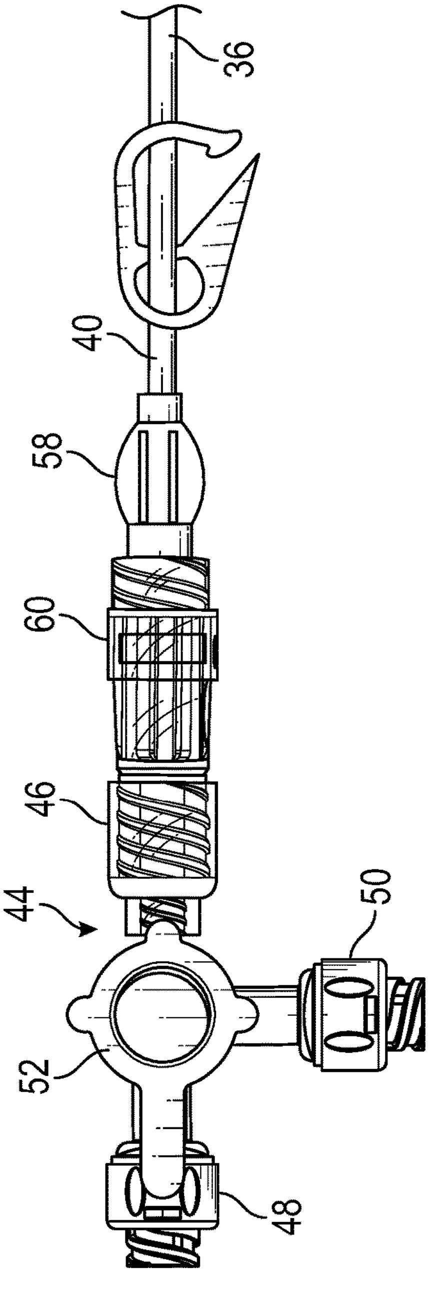
FIG. 2B is an upper perspective view of the catheter system, illustrating the three-way stopcock valve and an example needleless connector, according to some embodiments.
Figure 2C:
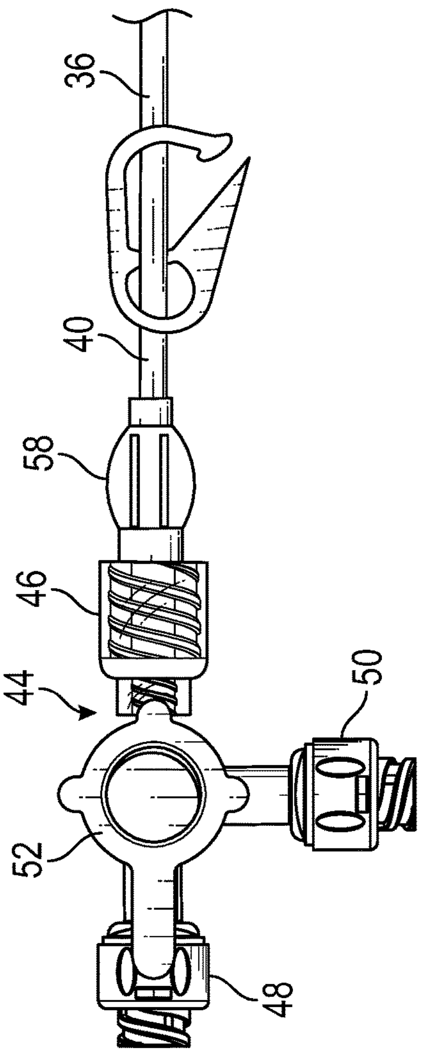
FIG. 2C is an upper perspective view of the catheter system, with the needleless access connector between the three-way stopcock valve and an example adapter, according to some embodiments.

Referring now to FIGS. 2B-2C, in some embodiments, the proximal end 40 of the extension tube 36 may be integrated with an adapter 58, which may be configured to couple to one or more of the pre-filled flush device 54, the temporary discard sample syringe 56, and the three-way stopcock valve 44. In further detail, in some embodiments, the proximal end 40 of the extension tube 36 may be permanently or non-removably coupled to the adapter 58, such as, for example, via adhesive, bonding, a non-luer coupling, or another suitable permanent or non-removable coupling. As illustrated in FIG. 2B, in some embodiments, the adapter 58 may be coupled to a needleless connector 60, which may reduce a risk of bacterial contamination. As referred to in the present disclosure, the term "needleless connector" may refer to the MAXZERO™ Needleless Connector (available from Becton, Dickinson & Company) or another suitable removable, needleless connector as is known in the art, which may be designed to reduce the risk of bacterial contamination.

Referring now to FIGS. 3A-3E, in some embodiments, the catheter system 10 may be compact, easing usage, and may improve workflow when collecting an arterial or venous blood sample. In some embodiments, a method of blood collection may include inserting the catheter 19 of the catheter system 10 into the blood vessel, such as a vein or artery, of the patient. In some embodiments, one or more steps of the method may be performed while monitoring arterial blood pressure via a pressure transducer and pressure monitoring system coupled thereto. In some embodiments, the method of blood collection may include coupling the pre-filled flush device 54 and/or the temporary discard sample syringe 56 to the catheter system 10. In some embodiments, the method may include closing the second port 48 (which may leave the third port 50 and the first port 46 open), as illustrated, for example, in FIG. 3A. In some embodiments, after closing the second port 48, the method may include pulling blood from the blood vessel into the temporary discard sample syringe 56. This may be accomplished by pulling a plunger of the temporary discard sample syringe 56. As illustrated, for example, in FIG. 3B, in some embodiments, after pulling blood into the temporary discard sample syringe 56, the method may include closing the first port 46. In some embodiments, after closing the first port 46, the method may include collecting blood in the blood sampling device 42, which may be coupled to the proximal port 30 of the three-port connector 26.

In some embodiments, the blood sampling device 42 may include a catheter advancement device configured to advance a secondary catheter to extend a life of the catheter 19 and/or provide blood sampling. In some embodiments, the catheter advancement device may include the PIVO™ Needle-Free Blood Collection Device, available from Becton, Dickinson & Company of Franklin Lakes, New Jersey, or another suitable catheter advancement device. In some embodiments, the method may include advancing the secondary catheter and/or a sensor of the catheter advancement device through the catheter 19 of the catheter system 10.

Figure 3A:
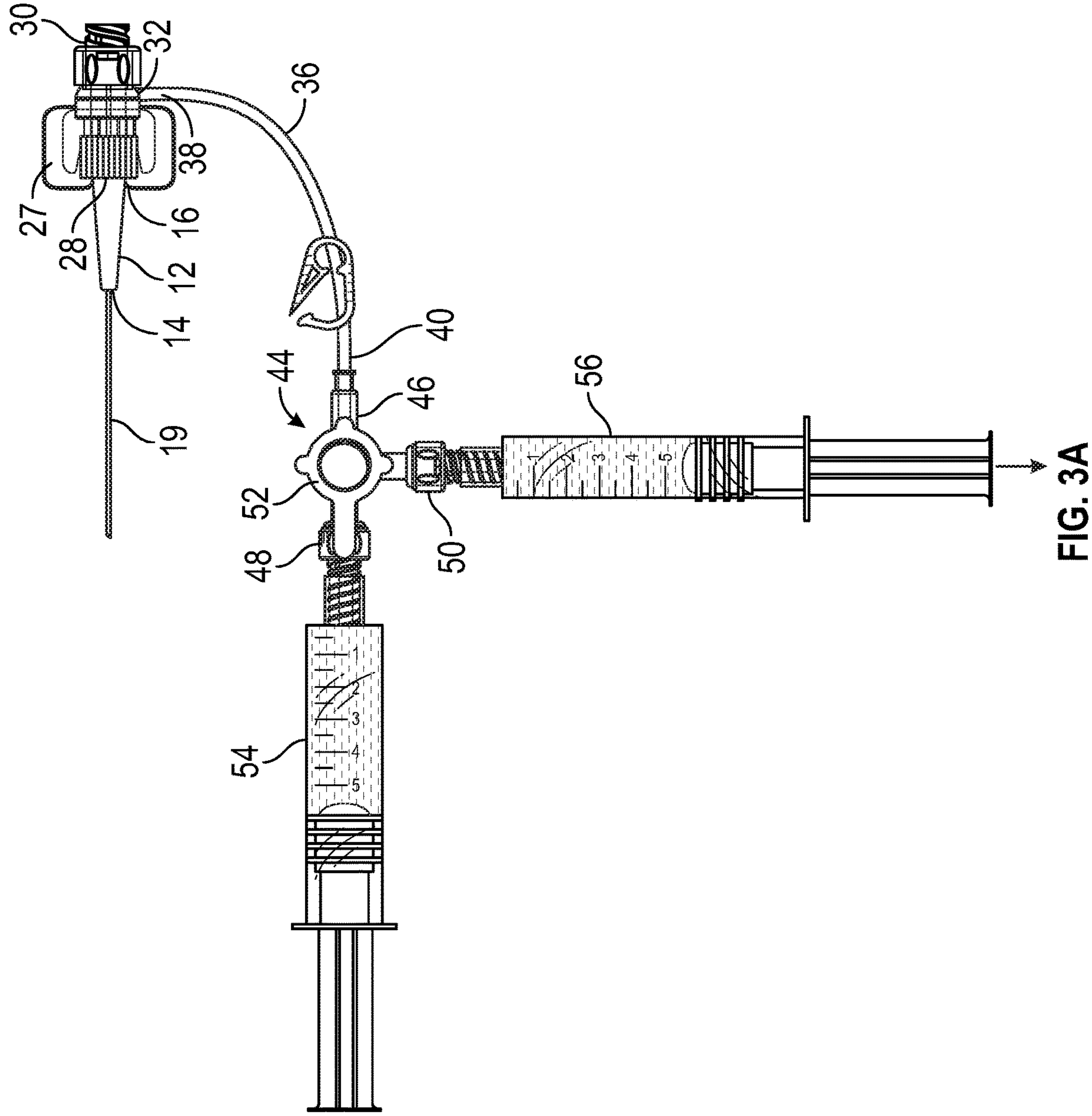
FIG. 3A is an upper perspective view of the catheter system, illustrating the temporary discard sample syringe when a temporary discard sample is taken, according to some embodiments.
Figure 3B:
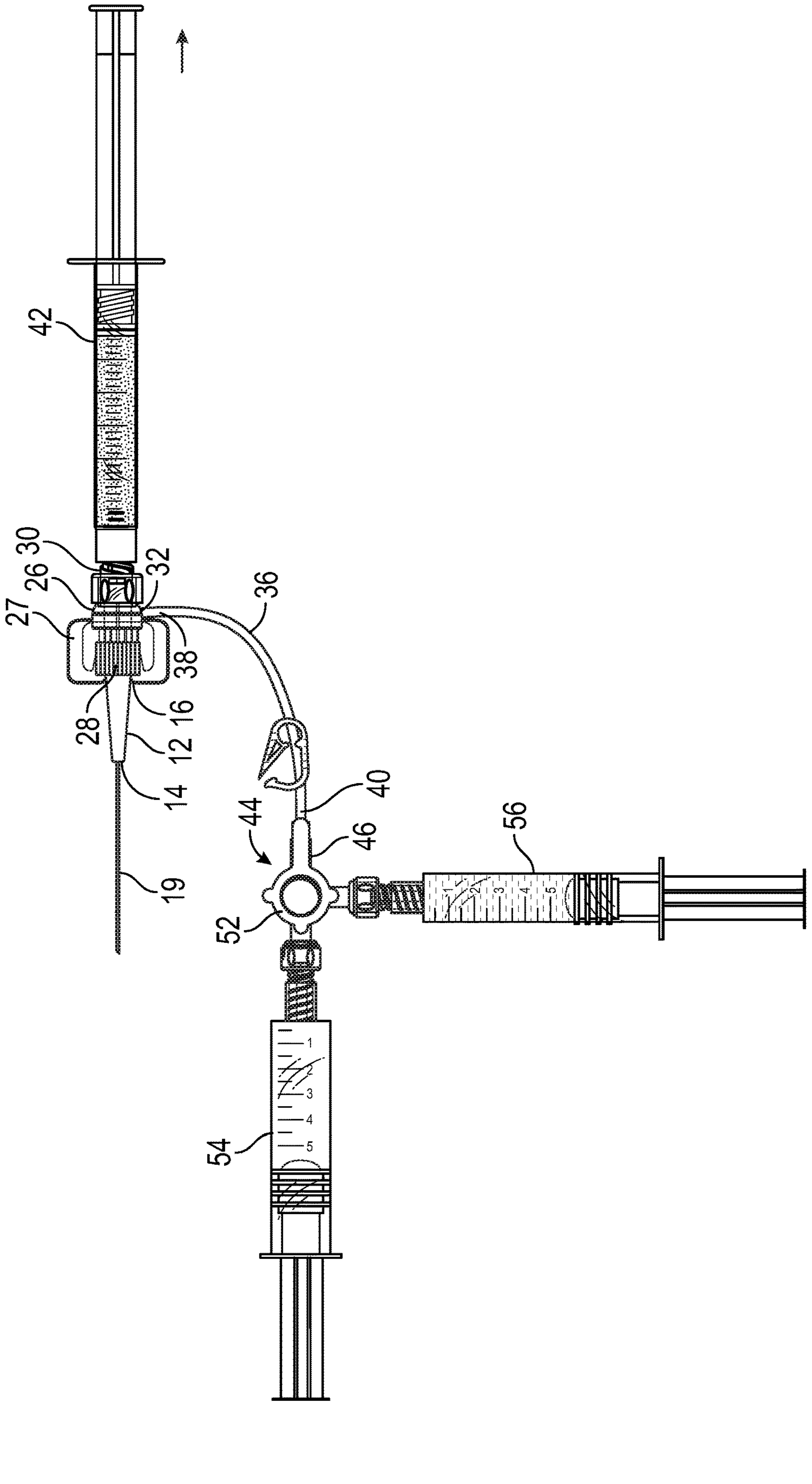
FIG. 3B is an upper perspective view of the catheter system, illustrating blood collection in an example blood sampling device, according to some embodiments.
Figure 3C:
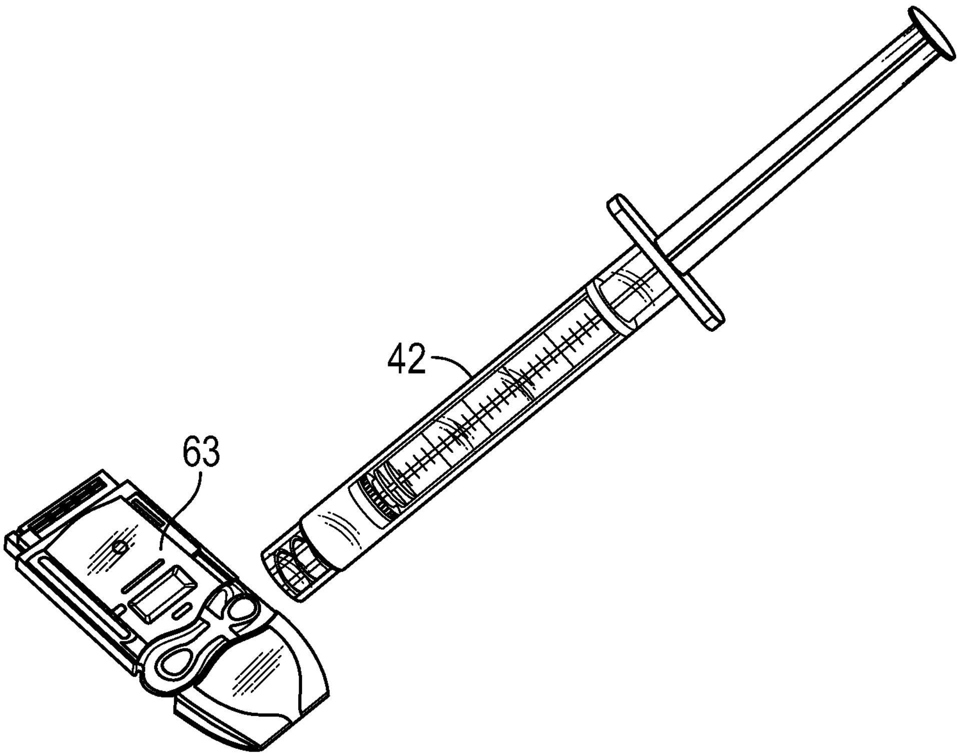
FIG. 3C is an upper perspective view of the catheter system, illustrating dispensing of blood from the blood sampling device onto an arterial blood gas (ABG) test cartridge for point of care (POC) blood testing, according to some embodiments.

As illustrated, for example, in FIG. 3C, in some embodiments, the blood sampling device 42 may include a heparinized syringe, and blood withdrawn into the heparinized syringe by withdrawing a plunger of the heparinized syringe may then be dispensed to an arterial blood gas (ABG) test cartridge for point of care (POC) blood testing.

Figure 3D:
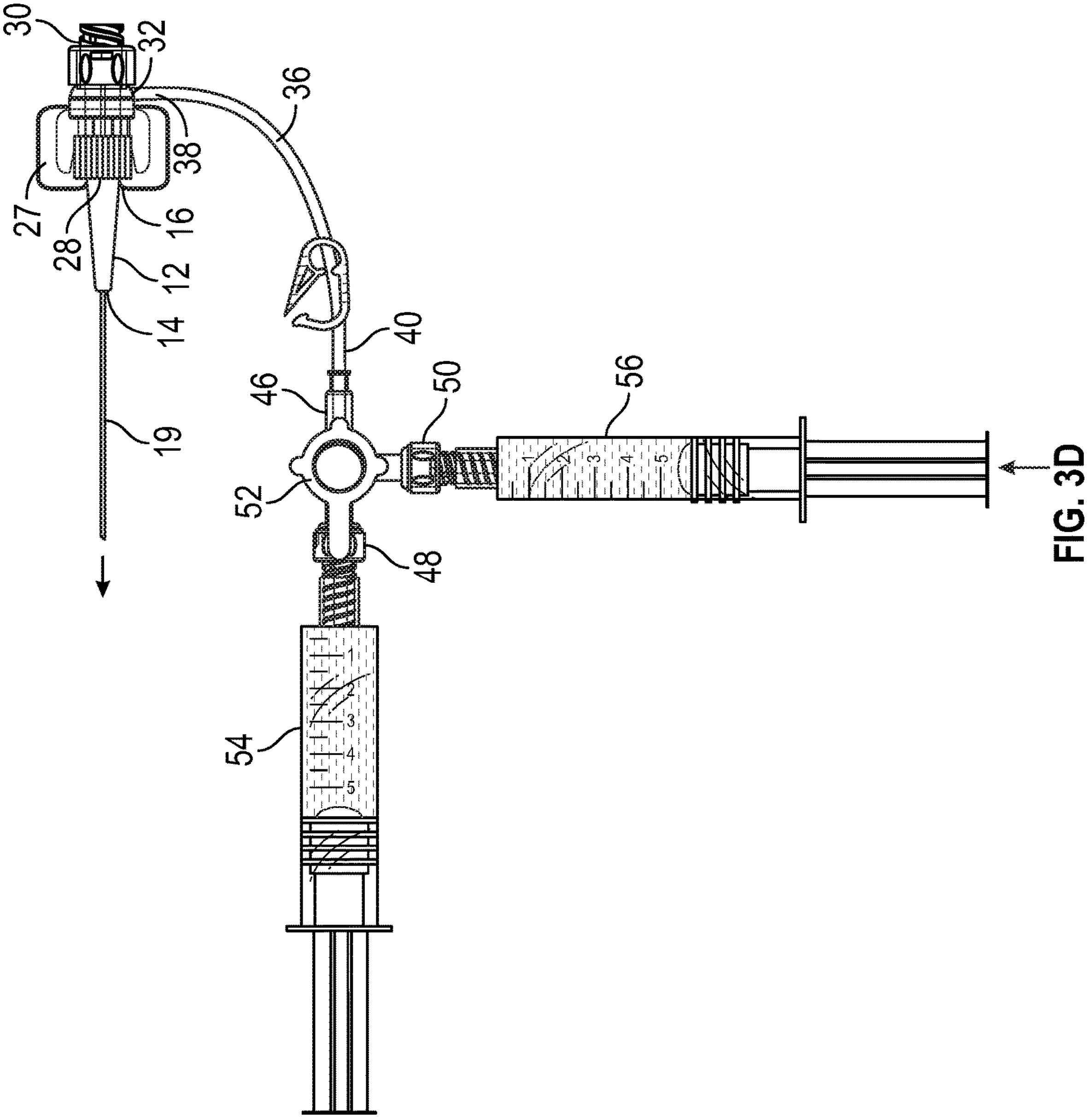
FIG. 3D is an upper perspective view of the catheter system, illustrating return of the blood pulled into the temporary discard syringe into a patient, according to some embodiments.

As illustrated, for example, in FIG. 3D, in some embodiments, after collecting blood in the blood sampling device 42 coupled to the proximal port 30 of the three-port connector 26, the method may include closing the second port 48 another time (which may leave the third port 50 and the first port 46 open). In some embodiments, after closing the second port 48 the other time, the method may include returning the blood pulled into the temporary discard sample syringe 56 into the patient, such as by depressing the plunger of the temporary discard sample syringe 56.

Figure 3E:
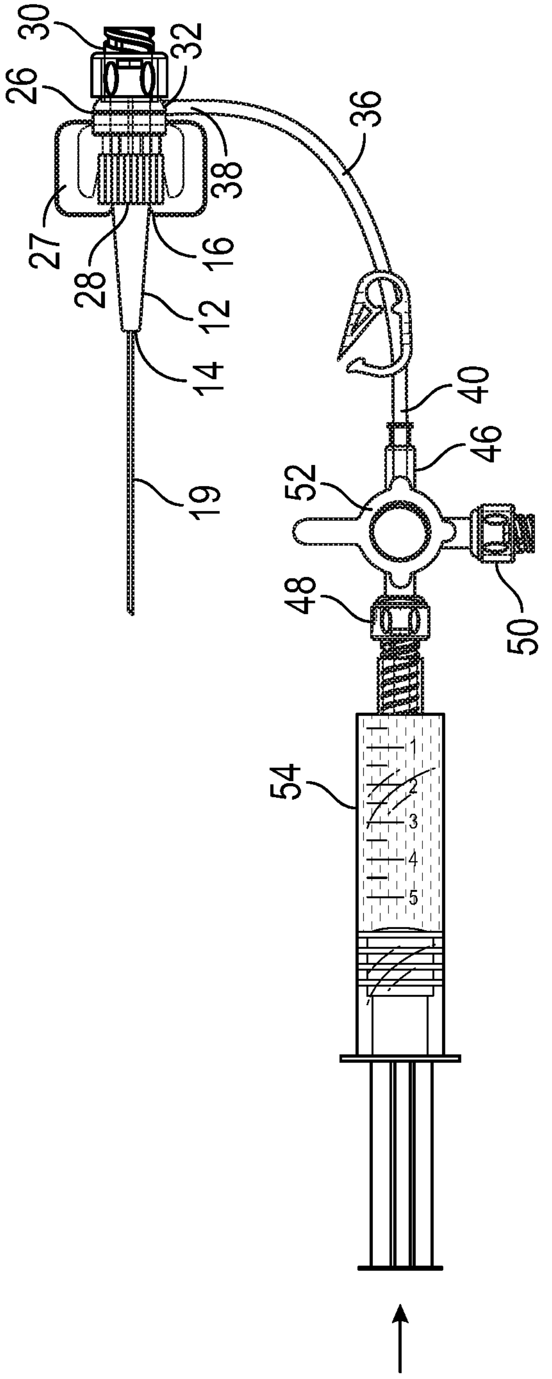
FIG. 3E is an upper perspective view of the catheter system, illustrating flushing of the catheter system, according to some embodiments.

As illustrated, for example, in FIG. 3E, in some embodiments, the method may include after returning the blood pulled into the temporary discard sample syringe 56 into the patient, turning the three-way stopcock valve 44 to an open position (such that each of the third port 50, the second port 48, and the first port 46 are open) and activating the pre-filled flush device 54 to clear the catheter system 10 with the single flush.

Figure 4A:
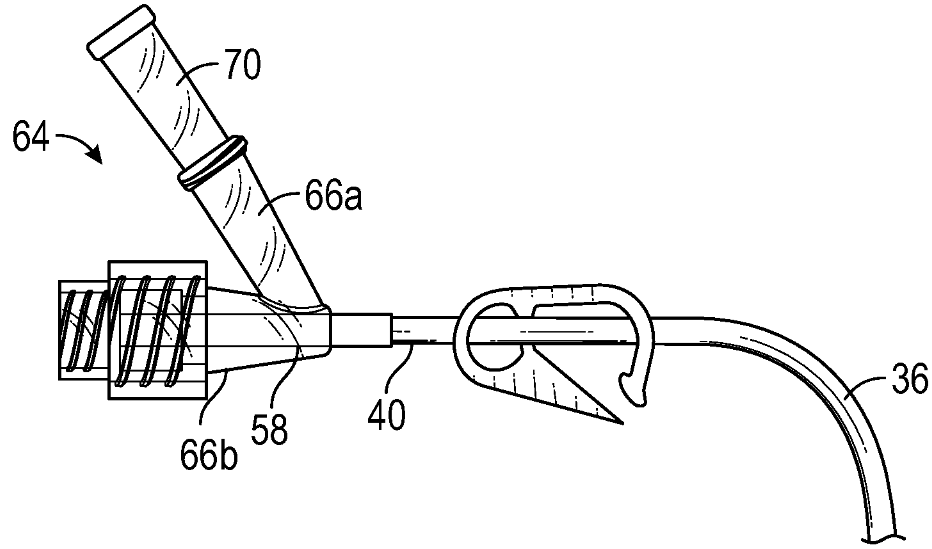
FIG. 4A is an upper perspective view of the catheter system, illustrating an example adapter that includes a proximal end having dual ports, according to some embodiments.

Referring now to FIGS. 4A-4D, in some embodiments, a proximal end 64 of the adapter 58 may include a single port or dual ports. In some embodiments, the proximal end 64 may include the dual port, which may include a luer port **66*a* and a luer port 66*b* (as illustrated in FIG. 4A, for example). In some embodiments, the dual ports may include a T-shape or a Y-shape. In some embodiments, the luer port 66*a* and/or the luer port 66*b* may include a female luer to facilitate removable coupling to another device. In some embodiments, a vent plug 70 may be disposed within the luer port 66*a*, which may allow venting of air but reduce a risk of bacterial contamination. In some embodiments, the luer port 66*b* may include a septum therein, which may reduce the risk of bacterial contamination. In some embodiments, the luer port 66*b*** may be coupled to a connector that may include a collar. In some embodiments, the collar may include one or more threads on the collar, and thus, the collar may facilitate a secure connection.

In some embodiments, one of the dual ports of the proximal end 64 may be coupled to the temporary discard sample syringe to temporarily withdraw a blood sample prior to blood sampling from the proximal port 30 of the three-port connector 26, to which a particular blood sampling device may be coupled (such as, for example, the PIVO™ Needle-Free Blood Collection Device, available from Becton, Dickinson & Company of Franklin Lakes, New Jersey). In some embodiments, after the blood sampling from the proximal port 30 of the three-port connector 26, the catheter system 10 may be cleared with the single flush by activating the pre-filled flush device. In some embodiments, another of the dual ports of the proximal end 64 may be coupled to the pre-filled flush device. In some embodiments, the dual ports may allow the temporary discard sample syringe and the pre-filled flush device to be coupled to the proximal end 64 at a same time.

In some embodiments, one or more of the dual ports may include a removable needleless connector coupled to a non-removable portion of a respective one of the dual ports. In some embodiments, the needleless connector may reduce a risk of bacterial contamination. In some embodiments, the pre-filled flush device and/or the temporary discard sample syringe may be coupled to the proximal end 64 via the needleless connector.

Figure 4B:
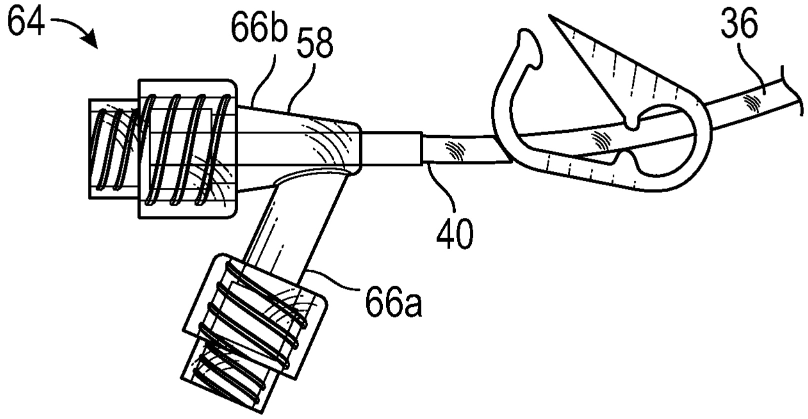
FIG. 4B is an upper perspective view of the catheter system, illustrating the adapter dual luer ports, according to some embodiments.

As illustrated in FIG. 4B, in some embodiments, the proximal end 64 may include the dual port, which may include two luer ports **66*a*, 66*b*. As illustrated, in some embodiments, the luer port 66*a* and/or the luer port 66*b* may be coupled to a connector that may include a collar. In some embodiments, the collar may include one or more threads on the collar, and thus, the collar may facilitate a secure connection. In some embodiments, the proximal end 64 of the adapter 58 and/or needleless connectors coupled thereto do not need to include ports that are compatible with the PIVO™ Needle-Free Blood Collection Device, because the PIVO™ Needle-Free Blood Collection Device or other catheter advancement device may be coupled to the proximal port 30 of the three-port connector 26 and may extend through the proximal port 30, the catheter adapter 12, and the catheter 19 to access the blood vessel for blood sampling. In some embodiments, an extended length of the extension tube 36 may decrease the risk of disturbing the insertion site when the user couples a device to the proximal end 64**.

Figure 4C:
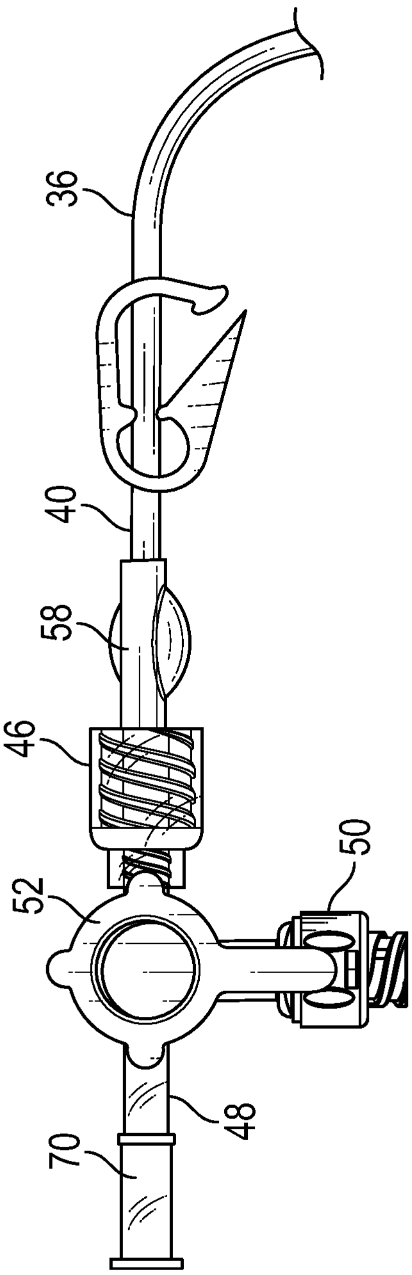
FIG. 4C is an upper perspective view of the catheter system, illustrating the three-way stopcock valve, according to some embodiments.
Figure 4D:
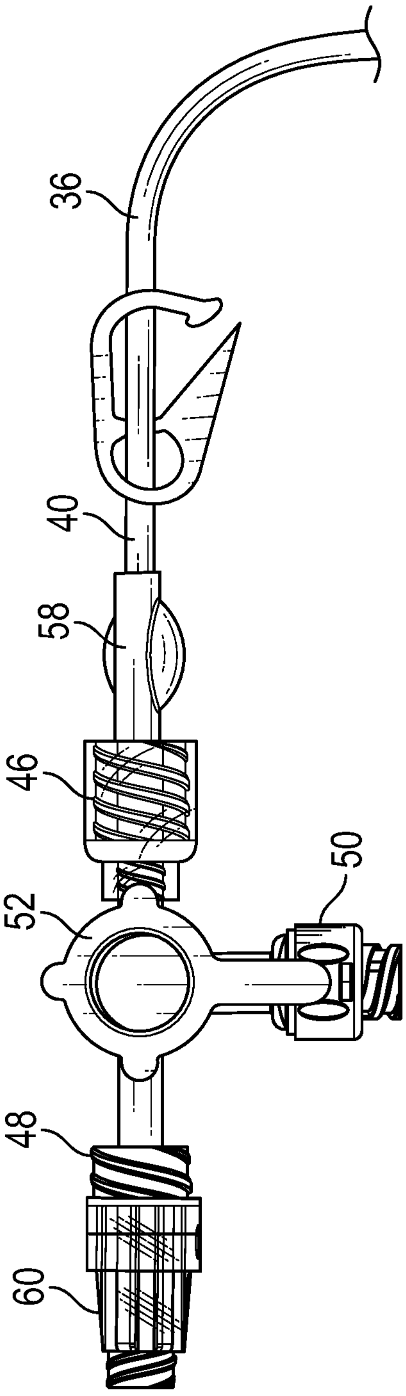
FIG. 4D is an upper perspective view of the catheter system, illustrating the three-way stopcock valve, according to some embodiments.

As illustrated in FIG. 4C-4D, in some embodiments, the first port 46 may include a luer, such as, for example, a female luer. In some embodiments, this may allow the needleless connector 60 (such as illustrated, for example, in FIG. 4D) to be coupled to and disposed between the first port 46 and the adapter 58, which may decrease a risk of bacterial contamination.

Figure 5B:
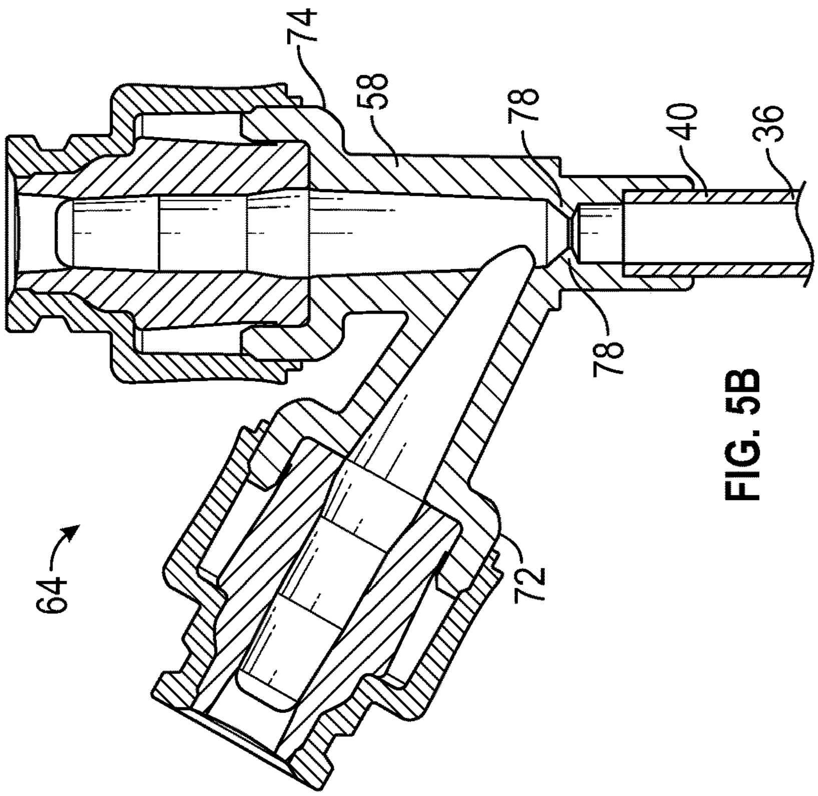
FIG. 5B is a cross-sectional view of the adapter, illustrating the proximal end having dual luer ports, according to some embodiments.
Figure 5A:
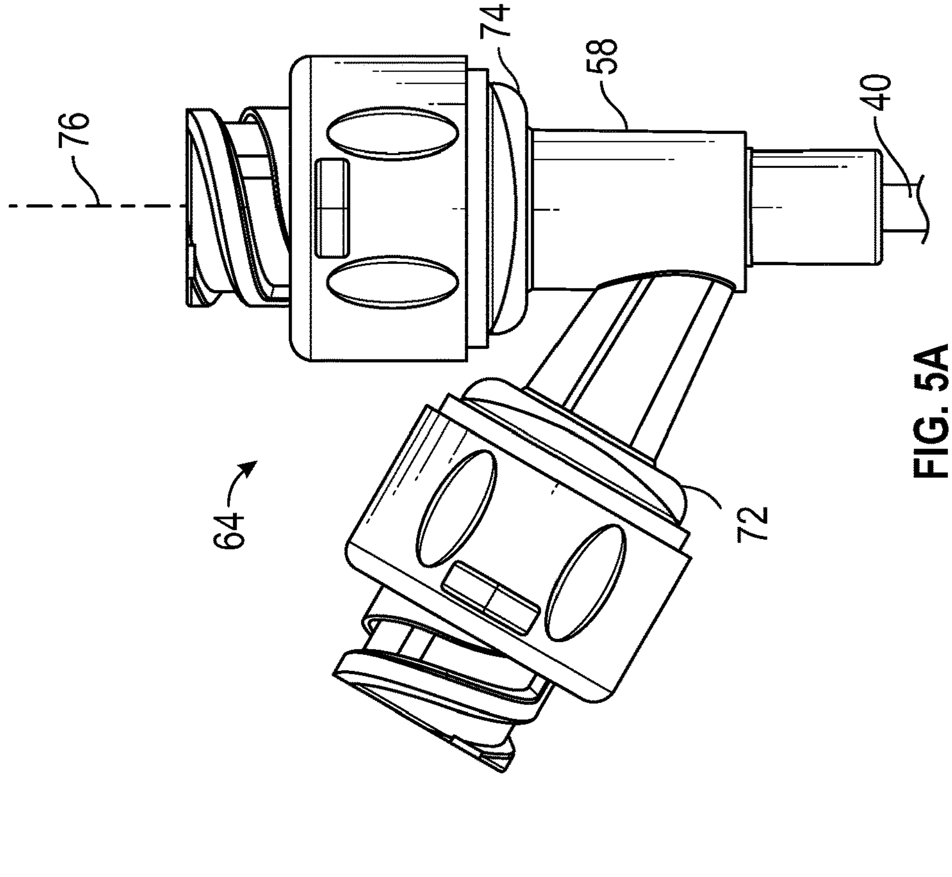
FIG. 5A is an upper perspective view of the adapter, illustrating the proximal end having dual luer ports, according to some embodiments.

Referring now to FIGS. 5A-5B, in some embodiments, the dual ports may include an offset side port 72 from an axial port 74 axially aligned with a longitudinal axis 76 of the adapter 58. In further detail, in some embodiments, the offset side port 72 may be non-planar with the axial port 74 and may facilitate flushing by creating turbulence. In some embodiments, the offset side port 72 may correspond to the luer port 66*a* of FIGS. 4A-4B and/or the luer port 66*b* of FIGS. 4A-4B in terms of one or more features and/or operation. In some embodiments, the axial port 74 may correspond to the luer port 66*a* of FIGS. 4A-4B and/or the luer port 66*b* of FIGS. 4A-4B in terms of one or more features and/or operation. In some embodiments, an inner lumen of the adapter 58 may include one or more fluid deflection ramps 78, which may create turbulence and enhance flushing. Additionally or alternatively, in some embodiments, the fluid deflection ramps 78 may be disposed within the three-way connector 26 to create turbulence and enhance flushing. In some embodiments, the fluid deflection ramps 78 may be disposed within the proximal port 30 of the three-way connector 26 to create turbulence and enhance flushing at a near-patient port. Example internal flushing feature(s) within the three-way connector 26 may include a feature, a wall, a channel, a flow path, a protrusion, and/or any other suitable feature configured to create turbulence, reduce an amount of priming volume, or reduce an amount of dead space within the three-way connector 26, and may be further described in U.S. Pat. No. 11,191,939, filed Nov. 30, 2018, entitled "STABILIZING CONNECTOR DEVICES FOR VASCULAR ACCESS AND METHODS OF USING THE SAME," which is hereby incorporated by reference in its entirety.

Figure 6A:
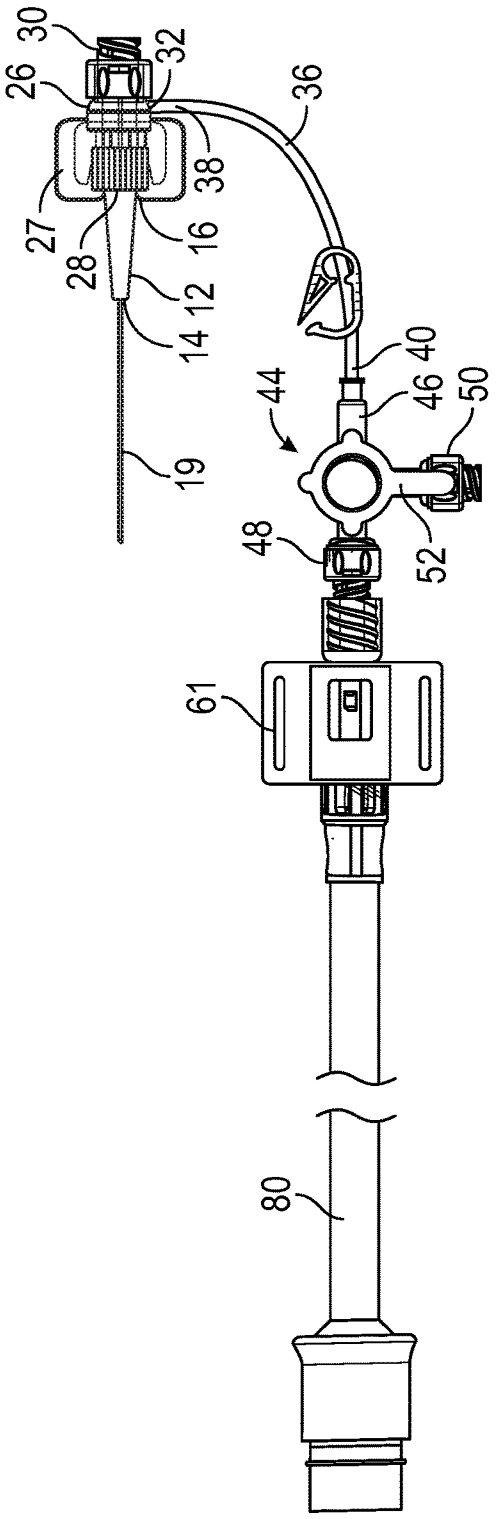
FIG. 6A is an upper perspective view of the catheter system, illustrating an example needleless connector coupled to an example pressure transducer, according to some embodiments.
Figure 6B:
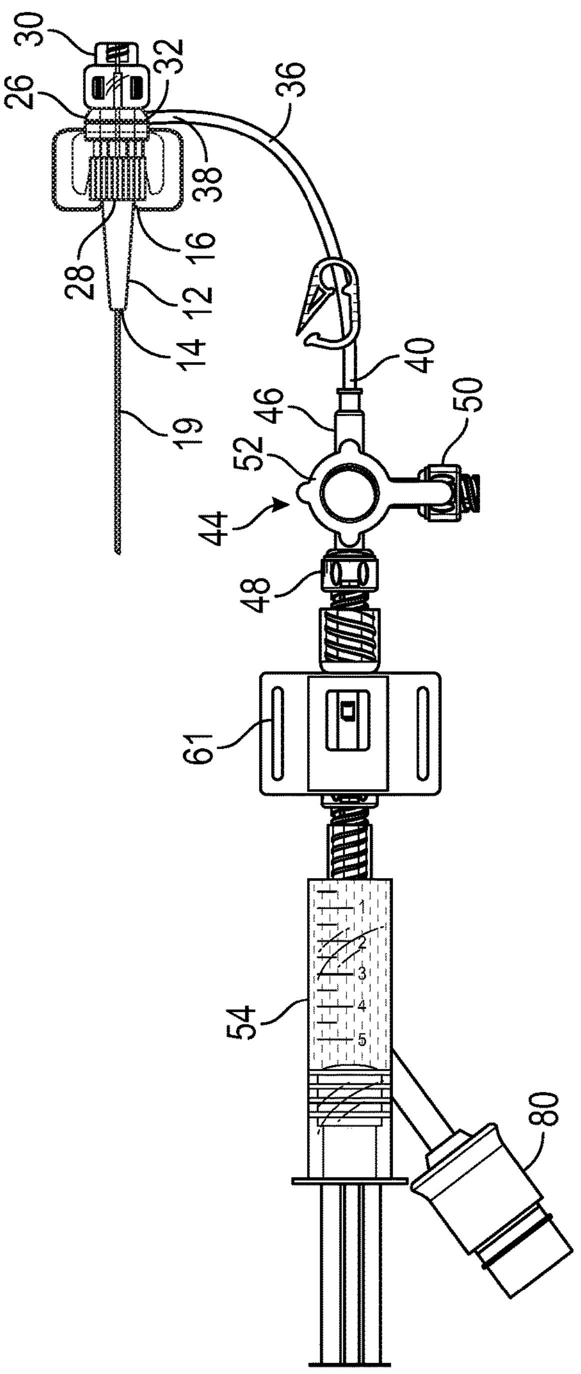
FIG. 6B is an upper perspective view of the catheter system, illustrating the example needleless connector between the pre-filled flush device and the pressure transducer, according to some embodiments.

Referring now to FIGS. 6A-6B, in some embodiments, the catheter system 10 may include the pressure transducer 62, which may be disposed between the second port 48 and the pre-filled flush device 54 or another suitable location. In some embodiments, the pressure transducer 62 may be included at any point along the fluid pathway of the catheter system 10. In some embodiments, the pressure transducer may include the TRANSPAC® IV Disposable Pressure Transducer (available from ICU Medical) or any other suitable pressure transducer. In some embodiments, the pressure transducer 62 may be disposed between the second port 48 and the pre-filled flush device 54, which may facilitate flushing of the catheter system 10 via a single flush. In further detail, in some embodiments, when the second port 48 is open, the temporary discard sample syringe 56 and blood sampling device 42 are removed, and the pre-filled flush device 54 is activated by depressing a plunger of the pre-filled flush device 54, fluid within the syringe may travel through the pressure transducer 62 and clear the second port 48, the third port 50, the first port 46, the extension tube 36, the three-port connector 26 (including the side port 32, the proximal port 30, and the distal port 28), the catheter adapter 12, and the catheter 19. In some embodiments, the fluid within the pre-filled flush device 54 may include saline or another suitable flush solution. In some embodiments, a configuration of the catheter system 10 to clear with the single flush may reduce an amount of the fluid needed for flushing.

In some embodiments, the pressure transducer 62 may be operatively coupled to a pressure transducer electrical connector 80, which may extend from the pressure transducer 62. In some embodiments, a proximal end of the pressure transducer 62 may be coupled to a needleless connector 60, which may reduce a risk of bacterial contamination. In some embodiments, the pre-filled flush device 54 may be coupled to the pressure transducer 62 or the needleless connector 60, which may facilitate flushing of the catheter system 10 via the single flush. In some embodiments, the pressure transducer 62 may be coupled to the third port 50 or another suitable location. In some embodiments, the pressure transducer 62 may be coupled to the third port 50 or the proximal port 30 of the three-port connector 26 to provide accurate measurements due to proximity to the blood vessel. In some embodiments, the needleless connector 60 and/or a fluid delivery line may be coupled to the pressure transducer 62. FIG. 6B illustrates the pre-filled flush device 54 coupled to a proximal end of the needleless connector 60, and FIG. 6A illustrates the proximal end of the needleless connector 60 free, according to some embodiments.

In some embodiments, the extension tube 36 may be rigid or semi-rigid and/or may include a particular or targeted thickness, which may provide sufficient stiffness or noncompliance to transmit a more accurate pressure pulse, resulting in a more accurate pressure measurement at the pressure transducer 62. In some embodiments, the pressure transducer 62 coupled to the three-way stopcock valve 44 may provide a benefit of monitoring arterial pressure at a point much closer to the patient than existing systems, which may facilitate a more accurate pressure measurement at the pressure transducer 62.

Figure 7:
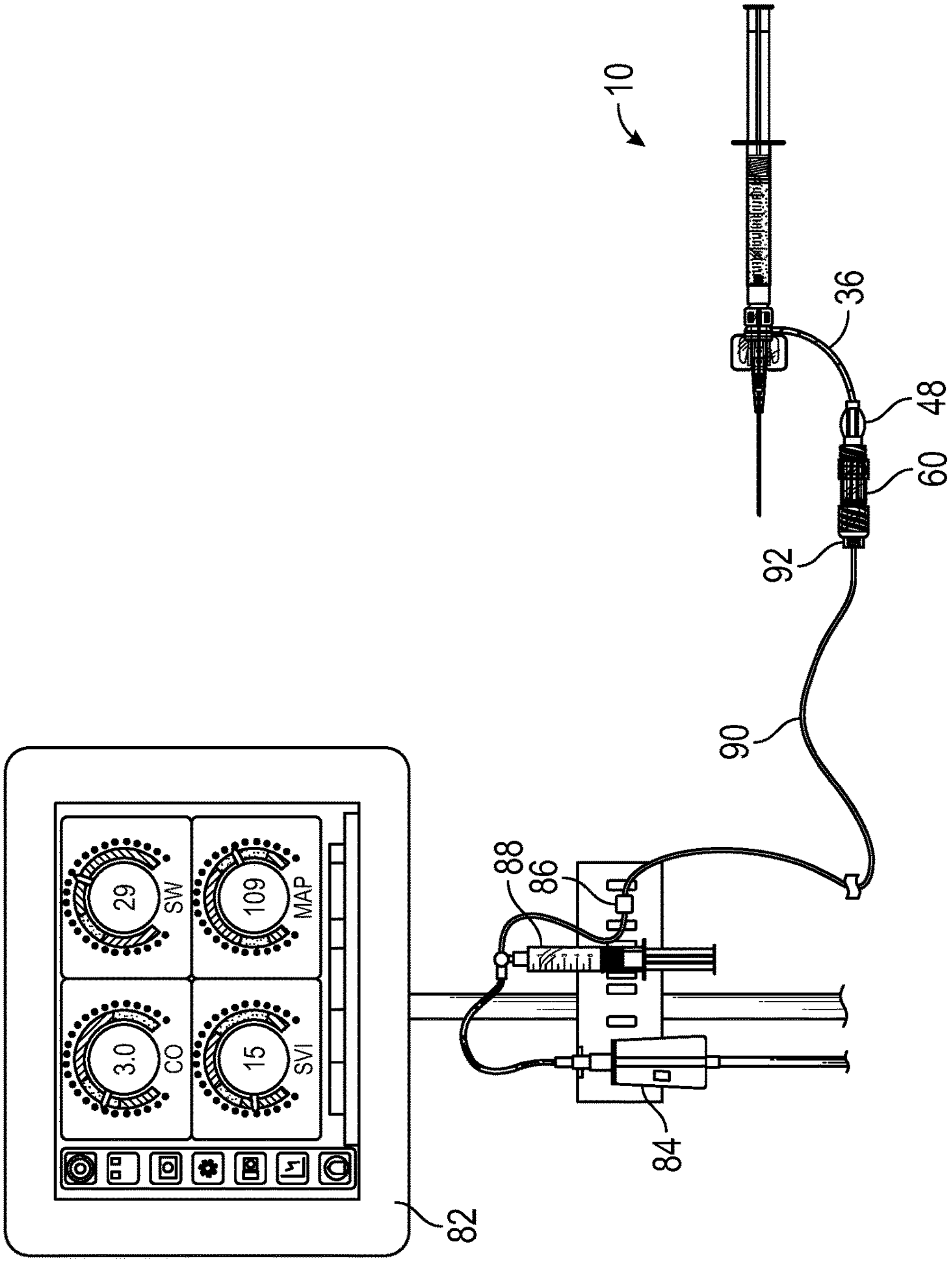
FIG. 7 is an upper perspective view of the catheter system coupled to a hemodynamic monitoring system, according to some embodiments.

Referring now to FIG. 7, the catheter system 10 is coupled to a hemodynamic monitoring system 82, which may be operatively coupled to one or more hemodynamic monitoring system sensors 84. In some embodiments, a second sampling port 86 may provide an alternate or additional location than the three-port connector 26 for blood sampling. In some embodiments, the second sampling port 86 may be used in perioperative and surgical settings. The second sampling port 86 may be eliminated due to presence of the three-port connector 26, negating a need for the second sampling port 86 in some embodiments.

In some embodiments, the temporary discard sample syringe 56 may be secured to the hemodynamic monitoring system 82 along with the hemodynamic monitoring system sensors 84, if desired. In some embodiments, a line 90, which may include pressure tubing, may be fluidically connected to the catheter system 10 via a connector 92.

Figure 8:
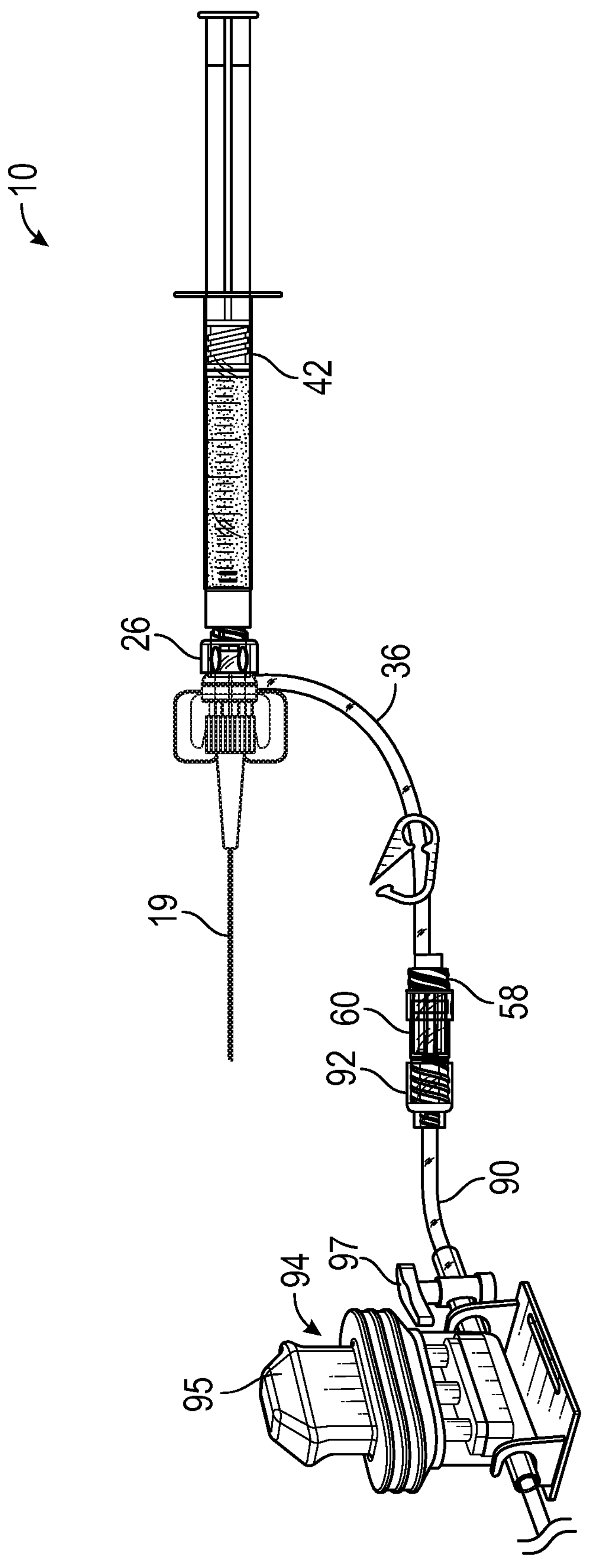
FIG. 8 is an upper perspective view of the catheter system coupled to a closed, near patient arterial blood sampling system, according to some embodiments.

Referring now to FIG. 8, in some embodiments, the line 90 may be coupled to a blood clearing system 94, which may be near patient and/or closed. In some embodiments, the blood clearing system 94 may be in-line and may facilitate collection of a temporary blood draw volume that may be later reinfused or pushed back into the patient. In some embodiments, after the temporary blood draw volume is collected within a reservoir of the blood clearing system 94 by raising a plunger 95 of the blood clearing system 94, a shutoff valve 97 may be closed, preventing fluid communication with the line 90 and aspiration of blood from the reservoir. In some embodiments, with the shutoff valve 97 closed, a blood sample may be collected from the proximal port 30 of the access connector 26. In some embodiments, the blood sample may be collected using the blood sampling device 42, which may include a catheter advancement device such as, for example, the PIVO™ Needle-Free Blood Collection Device, available from Becton, Dickinson & Company of Franklin Lakes, New Jersey. In some embodiments, after the blood sample is drawn, the shutoff valve 97 may be opened and the plunger 95 of the blood clearing system 94 may be depressed or pushed down to reinfuse the temporary blood draw volume within the reservoir into the patient. In some embodiments, the blood clearing system 94 within the catheter system 10 may not include a blood sampling port other than the proximal port 30 of the access connector 26, which may provide near-patient blood collection and may also facilitate use of the catheter system 10 with the catheter advancement device.

Figure 9:
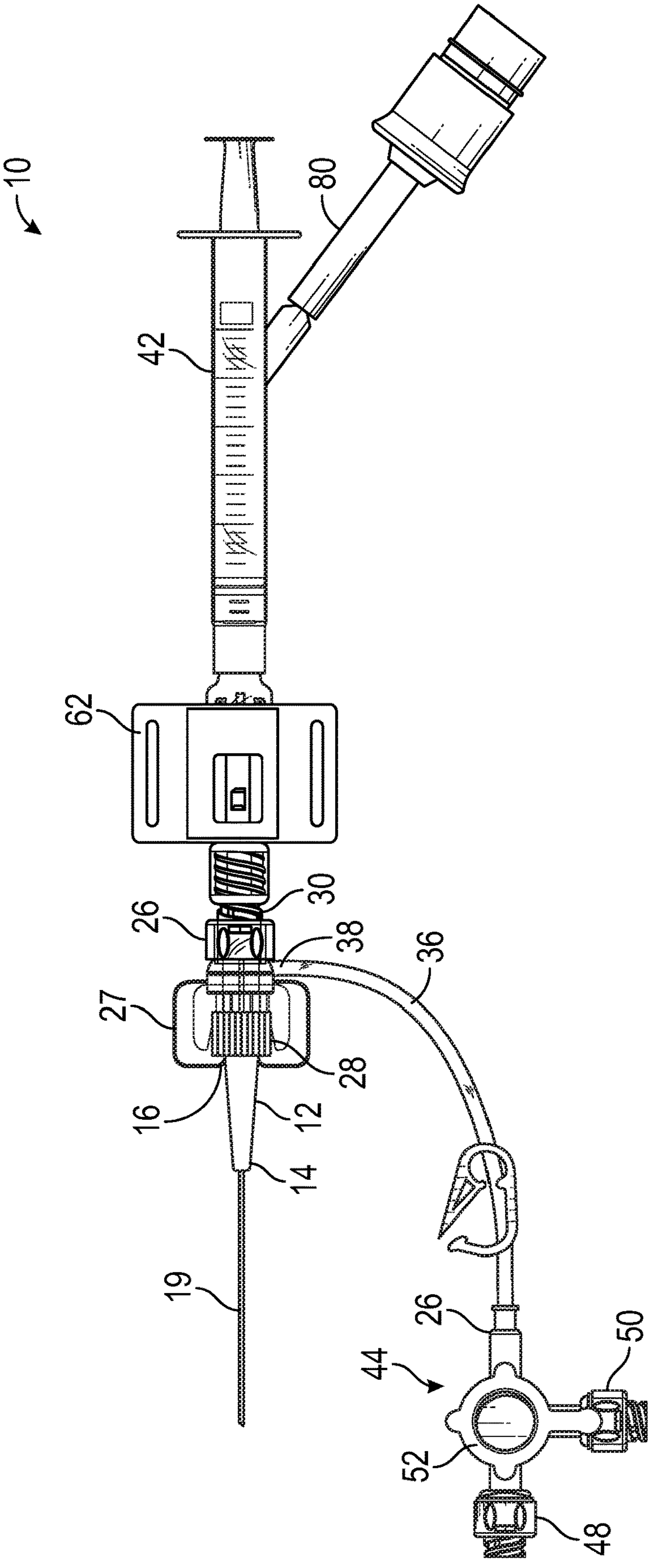
FIG. 9 is an upper perspective view of the catheter system, illustrating the pressure transducer, according to some embodiments.

Referring now to FIG. 9, in some embodiments, the pressure transducer 62 may be coupled to the proximal port 30, which may provide accurate pressure reading due to proximity to the catheter 19 and the blood vessel.

Figure 10:
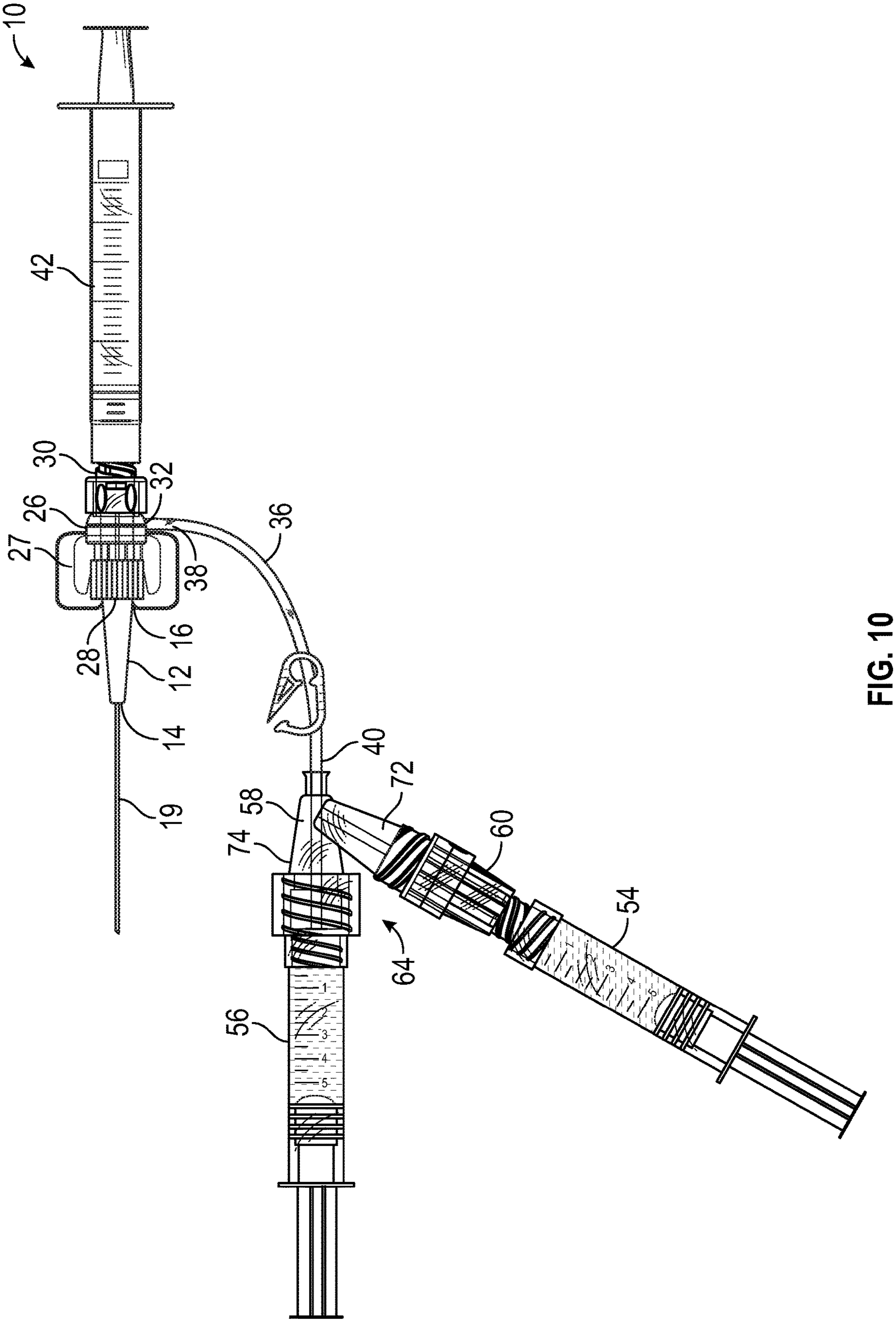
FIG. 10 is an upper perspective view of the catheter system, illustrating the pre-filled flush device and the temporary discard sample syringe coupled to the adapter, according to some embodiments.

Referring now to FIG. 10, in some embodiments, the pre-filled flush device 54 and the temporary discard sample syringe 56 may be coupled at a same time to the adapter 58, which may facilitate easy use for the clinician.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter system configured for blood sampling, comprising:

a catheter adapter, comprising a distal end, a proximal end, a lumen extending through the distal end of the catheter adapter and the proximal end of the catheter adapter;

a catheter extending from the distal end of the catheter adapter;

a three-port connector, comprising a distal port, a proximal port opposite the distal port, and a side port between the distal port and the proximal port, wherein the distal port and the proximal port are aligned with a longitudinal axis of the three-port connector, and wherein the proximal end of the catheter adapter is coupled to the distal port of the three-port connector; and an extension tube comprising a distal end and a proximal end, wherein the distal end of the extension tube is integrated with the side port of the three-port connector; and a three-way stopcock valve, wherein the three-way stopcock valve comprises a first port, a second port opposite the first port, and a third port, wherein the proximal end of the extension tube is coupled to the first port of the three-way stopcock valve, wherein the second port is configured to couple to a pre-filled flush device, wherein the third port is configured to couple to a temporary discard sample syringe, wherein the distal port, the proximal port, the side port, and the extension tube are in continual, fixed fluid communication such that blood may flow through a near-patient fluid pathway within the catheter, the catheter adapter, and the proximal port when the three-way stopcock valve is rotated to open fluid flow through the second port and to close fluid flow through the third port and when the three-way stopcock valve is rotated to open fluid flow through the third port and to close fluid flow through the second port.

2. The catheter system of claim 1, wherein the proximal port is monolithically formed as a single unit the distal port and the side port.

3. The catheter system of claim 1, further comprising a blood sampling device coupled to the proximal port.

4. The catheter system of claim 1, wherein the proximal end of the extension tube is integrated with the first port such that the extension tube is permanently coupled to the first port.

5. The catheter system of claim 1, wherein the catheter system comprises a fluid pathway within the catheter, the catheter adapter, the three-port connector, and the extension tube, wherein the second port, the third port, and the proximal port of the three-port connector are configured to provide access to the fluid pathway of the catheter system, wherein a portion of the fluid pathway comprises the near-patient fluid pathway.

6. The catheter system of claim 5, further comprising the pre-filled flush device coupled to the second port such that closing of the second port prevents fluid communication between the pre-filled flush device and the fluid pathway, and the temporary discard sample syringe coupled to the third port such that closing of the third port prevents fluid communication between the temporary discard sample syringe and the fluid pathway, wherein the temporary discard sample syringe is configured for temporary blood withdrawal.

7. The catheter system of claim 6, further comprising a pressure transducer disposed between the second port and pre-filled flush device.

8. The catheter system of claim 1, wherein the proximal end of the extension tube is integrated with an adapter, wherein the adapter is coupled to a needleless connector, wherein a proximal end of the adapter comprises a single port or a dual port.

9. A method of blood collection, comprising:

coupling a pre-filled flush device and a temporary discard sample syringe to a catheter system, wherein the catheter system comprises:

a catheter adapter, comprising a distal end, a proximal end, a lumen extending through the distal end of the catheter adapter and the proximal end of the catheter adapter;

a catheter extending from the distal end of the catheter adapter;

a three-port connector, comprising a distal port, a proximal port, and a side port between the distal port and the proximal port, wherein the distal port and the proximal port are aligned with a longitudinal axis of the three-port connector, wherein the proximal end of the catheter adapter is coupled to the distal port of the three-port connector;

an extension tube comprising a distal end and a proximal end, wherein the distal end of the extension tube is integrated with the side port of the three-port connector; and a three-way stopcock valve, wherein the three-way stopcock valve comprises a first port, a second port opposite the first port, and a third port, wherein the proximal end of the extension tube is coupled to the first port of the three-way stopcock valve, wherein the second port is coupled to the pre-filled flush device, wherein the third port coupled to the temporary discard sample syringe, wherein the distal port, the proximal port, the side port, and the extension tube are in continual, fixed fluid communication such that blood may flow through a near-patient fluid pathway within the catheter, the catheter adapter, and the proximal port when the three-way stopcock valve is rotated to open fluid flow through the second port and to close fluid flow through the third port and when the three-way stopcock valve is rotated to open fluid flow through the third port and to close fluid flow through the second port;

rotating the three-way stopcock valve to close fluid flow through the second port; and after rotating the three-way stopcock valve to close fluid flow through the second port, pulling blood into the temporary discard sample syringe.

10. The method of claim 9, further comprising:

after pulling blood into the temporary discard sample syringe, rotating the three-way stopcock valve to close fluid flow through the first port; and after rotating the three-way stopcock valve to close fluid flow through the first port, collecting blood in a blood sampling device coupled to the proximal port of the three-port connector.

11. The method of claim 10, wherein the blood sampling device comprises a catheter advancement device, further comprising advancing a secondary catheter of the catheter advancement device through the catheter.

12. The method of claim 10, further comprising:

after collecting blood in the blood sampling device coupled to the proximal port of the three-port connector, closing the second port another time; and after closing the second port the other time, returning the blood pulled into the temporary discard sample syringe into a patient.

13. The method of claim 12, further comprising:

after returning the blood pulled into the temporary discard sample syringe into the patient, turning the three-way stopcock valve to an open position and activating the pre-filled flush device to clear the catheter system with a single flush.

14. The method of claim 9, wherein the catheter system further comprises a pressure transducer disposed between the second port and pre-filled flush device.

15. A method of blood collection, comprising:

inserting a catheter system into a blood vessel of a patient, wherein the catheter system comprises:

a catheter adapter, comprising a distal end, a proximal end, a lumen extending through the distal end of the catheter adapter and the proximal end of the catheter adapter;

a catheter extending from the distal end of the catheter adapter;

a three-port connector, comprising a distal port, a proximal port, and a side port between the distal port and the proximal port, wherein the distal port and the proximal port are aligned with a longitudinal axis of the three-port connector, wherein the proximal end of the extension tube is integrated with the distal port of the three-port connector; and an extension tube comprising a distal end and a proximal end, wherein the distal end of the extension tube is integrated with the side port of the three-port connector; and advancing a secondary catheter of a catheter advancement device through the catheter, wherein the catheter advancement device is coupled to the proximal port of the three-port connector.

16. The method of claim 15, wherein the blood vessel is an artery.

17. The method of claim 15, wherein the catheter system further comprises a three-way stopcock valve, wherein the three-way stopcock valve comprises a first port, a second port opposite the first port, and a third port, wherein the proximal end of the extension tube is coupled to the first port of the three-way stopcock valve, wherein the catheter system further comprises a pressure transducer disposed between the second port and a pre-filled flush device.

18. The method of claim 17, further comprising monitoring arterial blood pressure via the pressure transducer while advancing the secondary catheter of the catheter advancement device through the catheter.

19. The method of claim 15, wherein the catheter system further comprises a three-way stopcock valve, wherein the three-way stopcock valve comprises a first port, a second port opposite the first port, and a third port, wherein the proximal end of the extension tube is coupled to the first port of the three-way stopcock valve, wherein a pressure transducer is coupled to the second port.

20. The method of claim 19, further comprising coupling a pre-filled flush device to the pressure transducer and activating the pre-filled flush device such that fluid from the pre-filled flush device flows through the pressure transducer.

* * * * *